United States Patent [19]

Rumburg

[11] Patent Number: 4,585,012
[45] Date of Patent: Apr. 29, 1986

[54] TONGUE MUSCULATURE MEASUREMENT AND STRENGTHENING APPARATUS

[76] Inventor: Lorri K. Rumburg, 211 Armstrong Ave., Frostburg, Md. 21532

[21] Appl. No.: 632,727

[22] Filed: Jul. 20, 1984

[51] Int. Cl.[4] .............................................. A61B 5/10
[52] U.S. Cl. .................................. 128/777; 128/25 R; 272/95
[58] Field of Search ............. 128/774, 777, 782, 25 R; 272/95; 73/379, 380, 381, 862.62, 849; 33/174 D

[56] References Cited

U.S. PATENT DOCUMENTS

| | | | |
|---|---|---|---|
| 1,363,534 | 12/1920 | Rogers | 272/95 |
| 1,944,601 | 1/1934 | Gulick | 33/174 |
| 1,953,088 | 4/1934 | Purdy | 272/57 |
| 1,976,639 | 10/1934 | Spitler | 33/174 |
| 2,382,289 | 8/1945 | Burt | 73/862.62 |
| 3,014,286 | 12/1961 | Hricak | 33/35 |
| 3,118,667 | 1/1964 | Barons | 272/79 |
| 3,800,782 | 4/1974 | Josephson et al. | 128/777 |

*Primary Examiner*—Kyle L. Howell
*Assistant Examiner*—Daniel Haneiwich

*Attorney, Agent, or Firm*—Harvey B. Jacobson

[57] ABSTRACT

An upright support is provided including a base at its lower end for stationary support relative to a stationary support surface. The upright includes a rear side rearwardly from which a collapsible chin rest projects at an elevation spaced slightly below the upper end of the upright and the front side of the upright mounts an upstanding blade therefrom deflectable both rearwardly and forwardly of the upright. The blade projects above the upper end of the upright and is engageable by the tongue of a patient whose chin is disposed on the chin rest rearward of the upright and an abutment member is slidable along the upright and the blade and is engageable by the latter with the abutment member serving as an adjustment member to vary the amount of forward thrust of a tongue on the blade required to forwardly deflect the blade upper end portion relative to the upright. A measuring device is provided for measuring and indicating the amount of forward deflection of the upper end of the blade as a result of a thrust being applied to the rear side thereof by the tongue of a patient whose chin is disposed on the chin rest.

7 Claims, 7 Drawing Figures

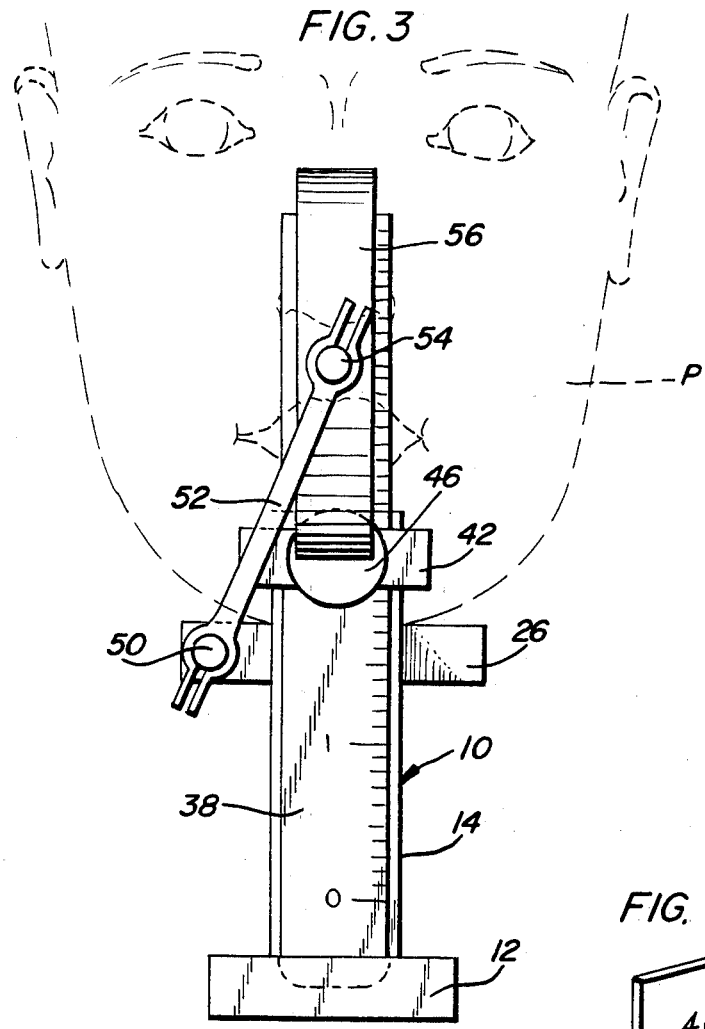
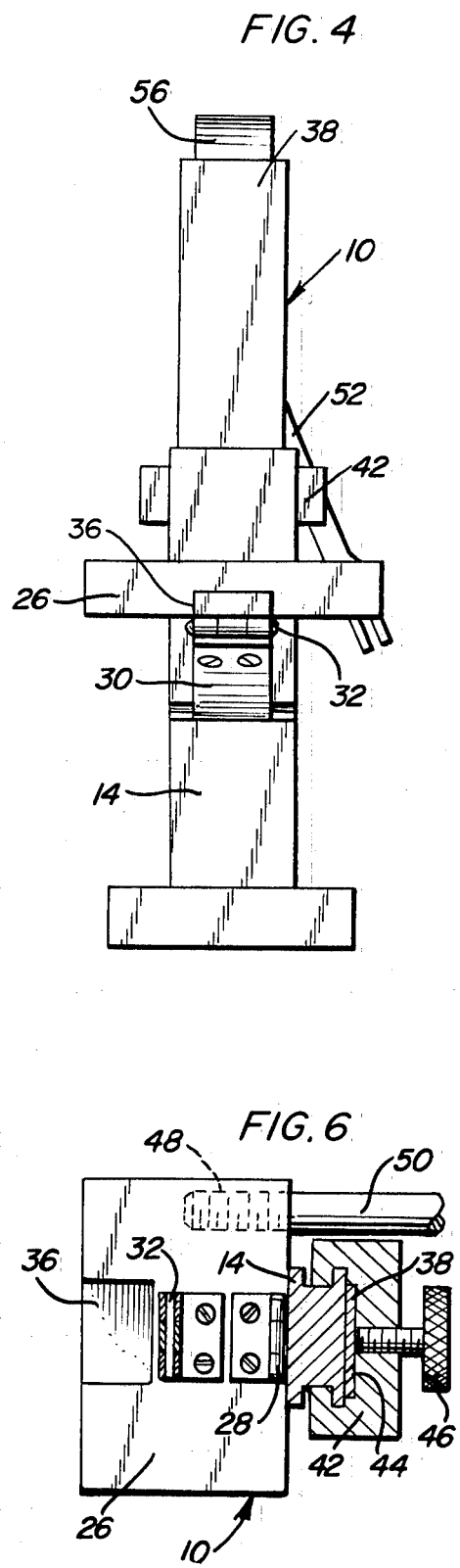
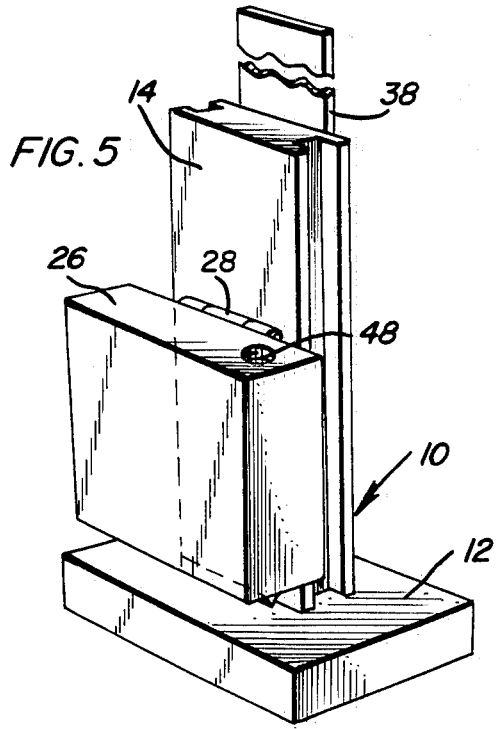
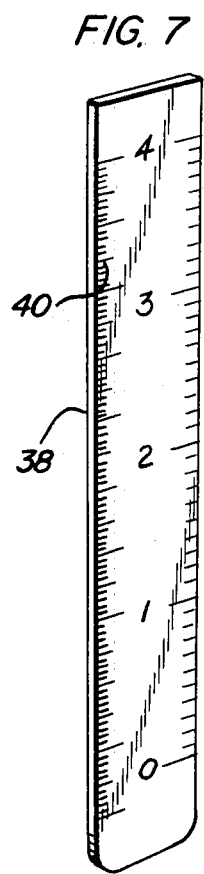

4,585,012

TONGUE MUSCULATURE MEASUREMENT AND STRENGTHENING APPARATUS

BACKGROUND OF THE INVENTION

The professions of speech pathology and neurology are involved with the assessment of strength and range of movement of various muscle groups. The examination of these muscle groups involves visual perusal and physical manipulation to determine deviations from normal.

This invention deals specifically and only with that portion of the neurological examination conducted by neurologists, or the peripheral oral examination done by speech pathologists which assess the strength of the tongue when protruded. Currently, tongue muscle strength is determined by having a patient push with his tongue against a wooden tongue blade held by the examiner. The examiner then judges, based upon past experience and intrinsic expectations, whether the muscle response is normal, weak or showing definite paresis.

Protrusion and lateralization of the tongue is accomplished mainly by the genioglossus muscle. Inervation of the tongue musculature is through the hypoglossal nerve. Muscle weakness suggests a disturbance or lesion along neural pathways. Individuals demonstrating tongue muscle weakness may have difficulty with the clear articulation of speech, and with swallowing.

As a component of many therapy procedures the speech pathologist desires to improve tongue strength and mobility as much as possible. This procedure is used with patients who suffer from some acquired neurological disorder, and also children and adults with cerebral palsy, individuals who habitually use a tongue thrust swallowing pattern, and occasionally with "simple" articulation cases where muscle weakness appears to interfere with therapy progress.

To increase muscle strength, isometric-type exercise is utilized. Patients push against a wooden tongue blade that they hold in hand. The strength of the patient produces a variable in the amount of resistance force they are able to sustain when holding the tongue blade. This invention provides a means of taking measurement of tongue strength along an arbitrary scale. The unit is positioned so that the patient is able to push a flexible metal (plastic or wood) blade away from in front of the mouth. The distance the tongue moves the blade indicates the strength of the muscle.

For building tongue strength, the patient uses a wooden tongue blade rather than the metal, or plastic blade. The isometric exercises assigned are performed against a uniform resistance. The amount of resistance can be varied by shifting an abutment member longitudinally of the blade.

Examples of various exercising and diagnostic apparatuses as well as measurement devices including some of the general structural and operational features of the instant invention are disclosed in U.S. Pat. Nos. 1,363,534, 1,944,601, 1,953,088, 1,976,639, 3,014,286, 3,118,667 and 3,800,782. However, these previously known devices are not specifically designed for exercising the tongue through the arrangement of component parts incorporating a chin rest together with a yieldable structure against which the tongue may be exercised and with the resistance to flexure of the yieldable member being adjustable and the yieldable member having a scale member operatively associated therewith.

BRIEF DESCRIPTION OF THE INVENTION

This invention relates to the measurement of the strengthening of the musculature of the tongue. The invention is designed to prove useful in peripheral oral examinations to aid in the accurate diagnosis of lingual weakness.

The invention includes a chin rest for locating the invention in a predetermined position relative to the patient and incorporates an upstanding yieldable blade supported at its lower end portion relative to the chin rest and including an upper end portion which is disposed slightly forward of and projects above the chin rest for engagement of the upper end of the blade by the tongue of the user of the apparatus.

The tongue is projected forwardly and engaged with the blade in order to forwardly deflect the upper end thereof and the amount of forward deflection of the upper end of the blade is measurable by scale means provided for this purpose. In addition, the apparatus includes a moment arm adjusting abutment member which may be shifted relative to the chin rest structure longitudinally of the blade and is contacted by the blade. By shifting the abutment member from the lower end portion of the blade toward the upper end portion of the blade the inherent resistance of the blade to forward deflection of the upper end portion thereof is increased. Of course, scale means may also be provided for predetermining the adjustment of the abutment member along the blade.

The main object of this invention is to provide an accurate and consistent measurement of lingual strength.

Another object of this invention is to provide an exercise apparatus which may be used to increase lingual strength.

Still another important object of this invention is to provide a device for testing tongue strength and mobility for diagnostic procedures to be used by both neurologists and speech pathologists.

Yet another object of this invention is to provide an apparatus whereby self-exercise of the tongue to increase the strength and mobility thereof may be carried out by a patient.

A final object of this invention to be specifically enumerated herein is to provide an apparatus in accordance with the preceding objects and which will conform to conventional forms of manufacture, be of simple construction and easy to use so as to provide a device that will be economically feasible, long lasting and relatively trouble free in operation.

These together with other objects and advantages which will become subsequently apparent reside in the details of construction and operation as more fully hereinafter described and claimed, reference being had to the accompanying drawings forming a part hereof, wherein like numerals refer to like parts throughout.

BRIEF DESCRIPTION OF THE DRAWINGS

FIG. 3 is a front elevational view of the apparatus;

FIG. 4 is a rear elevational view of the apparatus;

FIG. 5 is a fragmentary perspective view of the apparatus with the chin rest portion thereof in a folded position and the dial indicator structure removed therefrom;

FIG. 6 is a fragmentary horizontal sectional view taken substantially upon the plane indicated by the section line 6—6 of FIG. 2; and FIG. 7 is a perspective view of a typical metal or plastic flexure blade to be used in conjunction with the apparatus.

DETAILED DESCRIPTION OF THE INVENTION

Figure 1:
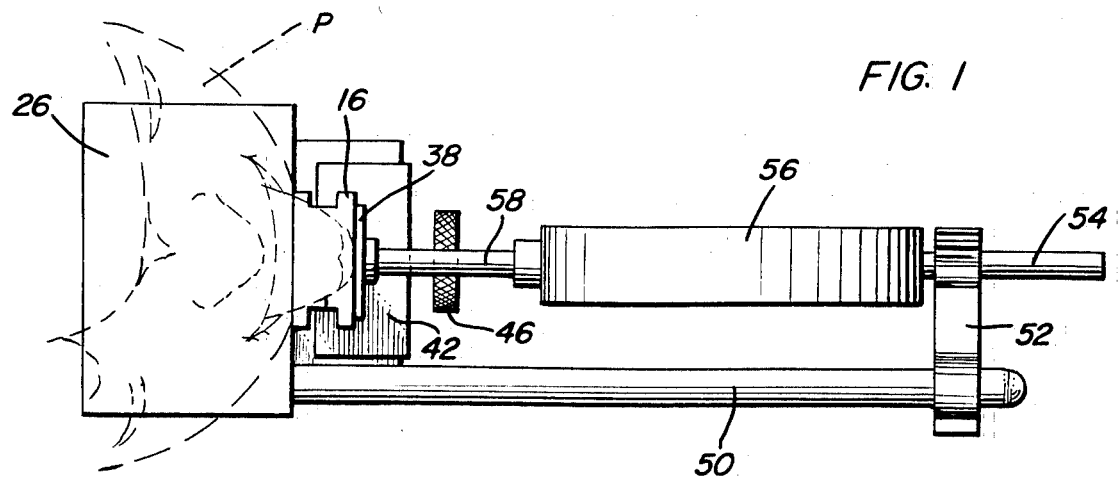
FIG. 1 is a top plan view of the apparatus of the instant invention.

Referring now more specifically to the drawings the numeral 10 generally designates the musculature measurement and strengthening apparatus of the instant invention. The apparatus 10 includes a base 12 which is portable but which may be anchored relative to a suitable support structure by any convenient means. Also, an upright support 14 of generally I-shaped cross-sectional shape has its lower end recessed and secured within a suitable socket (not shown) formed in the base 12. The upright support 14 includes an upper end portion 16, a lower end portion 18 supported from the base 12 and an intermediate height portion 20 as well as front and rear sides 22 and 24.

A chin rest block 26 is pivotally supported by a hinge 28 from the intermediate height portion 20. The chin rest block 26 projects rearward from the rear side 24 of the support 14 and includes a prop 30 pivotally supported therefrom by a hinge 32 and the intermediate height portion 20 includes a rearwardly opening recess 34 formed therein in which the free end of the prop 30 is engageable to releasably prop the chin rest block 26 in the horizontal position thereof illustrated in FIG. 2. The prop 30 is disengageable from the recess 34 and swingable approximately 120° in a clockwise direction as viewed in FIG. 2 toward a position with the prop 30 partially recessed within a recess 36 provided therefor in the block 26 in order to enable the chin rest block 26 to be swung to the vertically disposed retracted position thereof illustrated in FIG. 5.

The base 12 also removably supports the lower end of an upright resilient and flexive metal, or plastic blade 38 therefrom with the blade 38 abutted against and extending upwardly along the front side 22 of the support 14. The blade 38 includes scale indicia 40 extending there along and an abutment member in the form of a generally channel-shaped fulcrum member 42 is slidably mounted on the forward portion of the upright support 14 for vertical adjustment there along and includes a guideway 44 formed therein in which the blade 38 is slidably received. In addition, the abutment or fulcrum member 42 includes a setscrew 46 threadedly supported therefrom for clampingly engaging the blade 38 between the setscrew 46 and the upright support 14.

Figure 2:
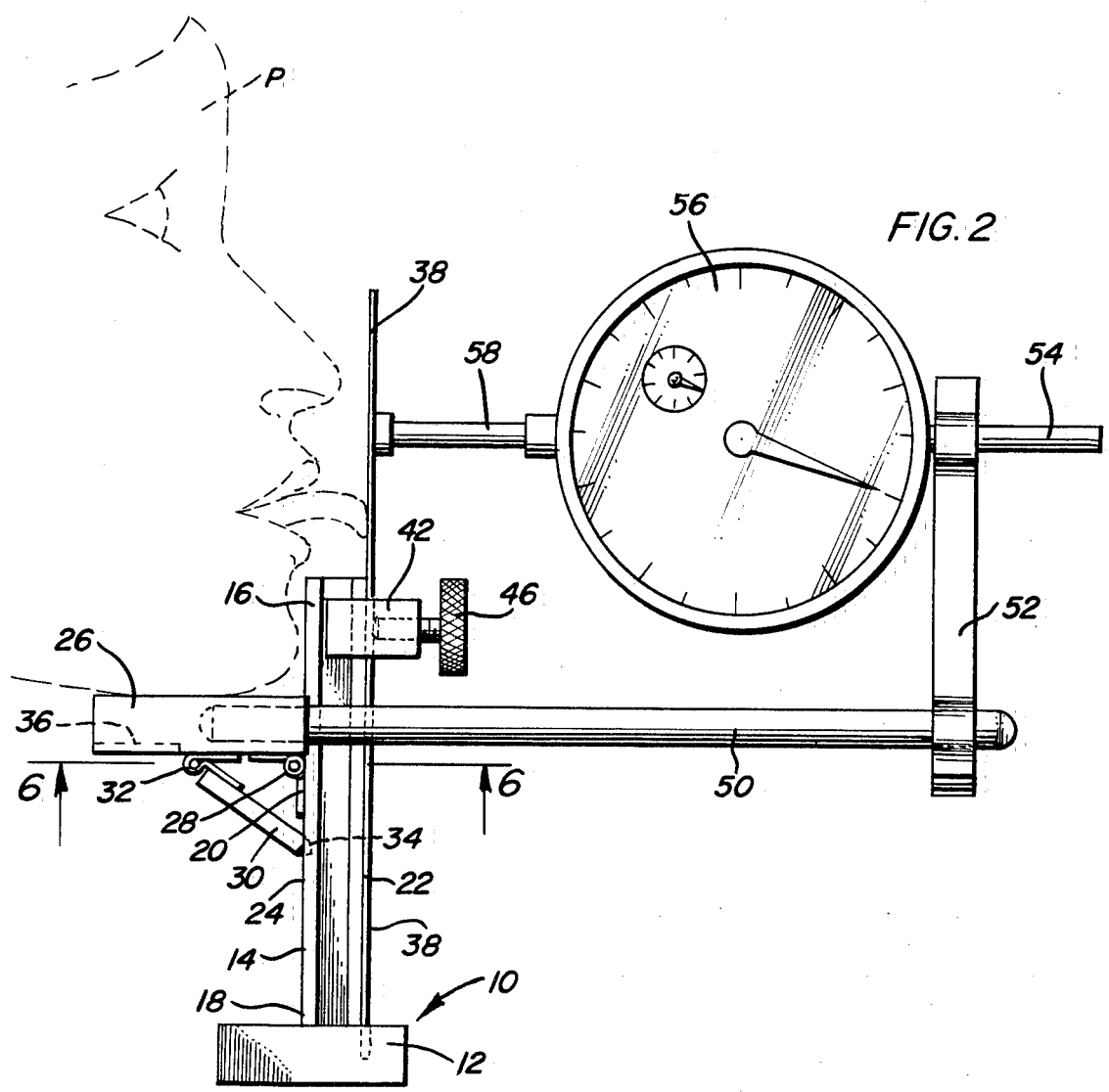
FIG. 2 is a side elevational view of the apparatus.

The end of the chin rest block 26 which faces forwardly when the block 26 is in the horizontal position thereof illustrated in FIG. 2 includes a threaded blind bore 48 formed therein and the bore 48 opens forwardly at a location spaced slightly to one side of the upright support 14. The threaded rear end of a support rod 50 is removably threadedly engaged in the bore 48 and the forward end of the rod has one end of a support arm 52 clamped engagingly supported therefrom in adjusted angular position on the rod 50. The other end of the support arm 52 mounts the mounting shank portion 54 of a dial indicator 56 and the dial indicator 56 includes a reciprocal operating plunger 58 registered with and abutted against the front side of the upper end portion of the blade 38.

The support rod 50 and bore 48 are provided with right hand threads and the support arm 52 mounts the shank 54 of the dial indicator 56 in cantilever fashion whereby the weight of the dial indicator 56 supported from the support arm 52 will tend to turn the support rod 50 in a direction to tighten the threaded connection between the support rod 50 and the chin rest block 26. In addition, in lieu of the dial indicator 56 a simple spring returned bell crank lever incorporating a protractor type pointer arm and protractor scale could be used. Further, any suitable digital readout indicator also could be used in lieu of the dial indicator 56. Further, the dial indicator and blade 38 may include either English or metric scales thereon and the dial indicator 56 may be rotated in a manner such that the dial portion thereof may face in substantially any direction.

In operation, a patient P may have his or her head positioned in the manner illustrated in FIGS. 1, 2 and 3 of the drawings with the patient's chin resting upon the upper surface of the chin rest block 26 and abutted against the rear side 24 of the upright support or standard 14. Then, the tongue of the patient is extended, engaged with and utilized to forwardly displace the upper end portion of the blade 38. The height of the abutment or fulcrum member 42 along the upright support 14 and the blade 38 will determine the amount of tongue strength which is required to forwardly displace the upper end portion of the blade 38 a predetermined amount and the dial indicator 56 is operative to measure the amount of forward displacement of the blade 38. Accordingly, adjustment of the abutment member 42 may be used to adapt the apparatus for use in conjunction with substantially all patients to be tested.

If it is desired to gain a measure of lateral tongue strength, the chin of the patient P is disposed on the chin rest block 26 with the medial plane of the apparatus 10 disposed at right angles to the medial plane of the head of the patient P. In this manner, lateral protrusion and strength of the tongue of the patient P may be tested. Of course, lateral tongue strength to either side may be tested by first testing lateral tongue strength to one side of the head of the patient P and then testing lateral tongue strength to the other side of the head of the patient P.

In addition to being usable as a testing and diagnostic apparatus, the apparatus 10 further may be used as a tongue exercising device to be used by the patient P on a scheduled basis. In such case the dial indicator 56 will be of a type whereby the dial thereof may be readily viewed by the patient P. In this manner, the patient P may view his own progress in tongue strength development.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as new is as follows:

1. A tongue musculature measurement and strengthening apparatus, said apparatus including a support having front and rear sides and upper and lower marginal portions, a horizontal chin rest supported from said upper marginal portion below the upper marginal portion below the upper terminal end thereof and projecting rearwardly of said support, an elongated spring blade having opposite side surfaces facing forwardly and rearwardly of said support and including base and free ends, means stationarily mounting said base end from said support with said blade positioned with the free end of said blade spaced above and forward of said chin rest for engagement by the free end of the tongue of a patient having his or her chin resting upon said chin rest and disposed immediately rearward of said upper marginal portion, said free end of said blade being forwardly displaceable relative to said support as a result of sufficient forward tongue pressure applied there against from the rear facing side surface thereof, and abutment means mounted from said support for adjusted shifting relative thereto longitudinally of said blade between said base and free ends and closely overlying the forwardly facing surface of said blade to thereby adjust the effective moment arm length of said blade between said abutment means and said blade free end portion and measurement means operative to indicate the amount of forward deflection of said free end of said blade as a result of forward tongue pressure thereon.

2. The apparatus of claim 1 wherein said chin rest is horizontally elongated in a front-to-rear extending direction and is pivotally supported from said support for downward swinging of the rear end of said chin rest toward a collapsed vertical position disposed rearward of said support.

3. The apparatus of claim 1 wherein said measurement means includes gauge means operative to indicate the amount of forward deflection of said free end of said blade as a result of forward tongue pressure thereon.

4. The apparatus of claim 3 wherein said gauge means includes a dial indicator.

5. The apparatus of claim 1 wherein said apparatus includes means operative to indicate predetermined adjusted positions of said abutment means longitudinally of said blade.

6. The apparatus of claim 1 wherein said elongated blade is disposed in upright position with said base end lowermost.

7. The apparatus of claim 6 wherein said chin rest is horizontally elongated in a front-to-rear extending direction and is pivotally supported from said support for downward swinging of the rear end of said chin rest toward a collapsed vertical position disposed rearward of said support.

* * * * *